United States Patent [19]

Morrow et al.

[11] Patent Number: 4,596,556
[45] Date of Patent: Jun. 24, 1986

[54] HYPODERMIC INJECTION APPARATUS

[75] Inventors: J. Thomas Morrow, Beaverton; Eugene C. Covey, Portland, both of Oreg.

[73] Assignee: Bioject, Inc., Portland, Oreg.

[21] Appl. No.: 715,930

[22] Filed: Mar. 25, 1985

[51] Int. Cl.[4] ............................................. A61M 5/30
[52] U.S. Cl. .................................................. 604/70
[58] Field of Search .................. 604/70, 71, 68, 137, 604/140, 218

[56] References Cited

U.S. PATENT DOCUMENTS

| | | | |
|---|---|---|---|
| 2,737,946 | 3/1956 | Hein, Jr. | 604/70 |
| 2,764,977 | 10/1956 | Ferguson | 604/70 |
| 3,688,765 | 9/1972 | Gasaway | 604/70 |
| 3,695,266 | 10/1972 | Lussier | 604/70 |
| 3,853,125 | 12/1974 | Clark et al. | 604/70 |
| 4,329,988 | 5/1982 | Sarnoff et al. | 604/137 |
| 4,403,989 | 9/1983 | Christensen et al. | 604/137 |

*Primary Examiner*—John D. Yasko
*Attorney, Agent, or Firm*—Kolisch, Hartwell & Dickinson

[57] ABSTRACT

The present invention provides a pressure-operated hypodermic injection apparatus which is particularly suitable for needleless operation. The apparatus includes an elongate shell having an inwardly facing wall with a uniform configuration along a defined length thereof, with the shell further defining a discharge aperture adjacent one end thereof. It further includes a plunger which is slideably disposed within the defined length of the shell, and which is shiftable between a ready position and a spent position, with the spent position being closer to the aperture than the ready position. With the plunger in its ready position, the shell and plunger collectively define an ampule chamber which is capable of containing a dischargeable medication. A pressurized-gas cartridge is mounted to the plunger to shift therewith, and has gas-releasing means which faces away from the discharge aperture. A body is further included which is sealingly and releasably joined to the other end of the shell. An actuator is mounted to the body and is manually operable for selectively operating the gas-releasing means to drive the plunger from its ready toward its spent position to discharge medication from the apparatus and into the patient.

29 Claims, 10 Drawing Figures

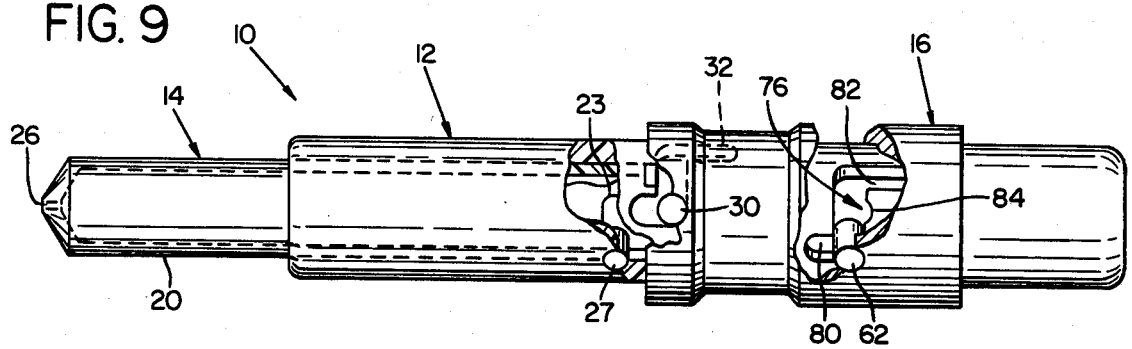
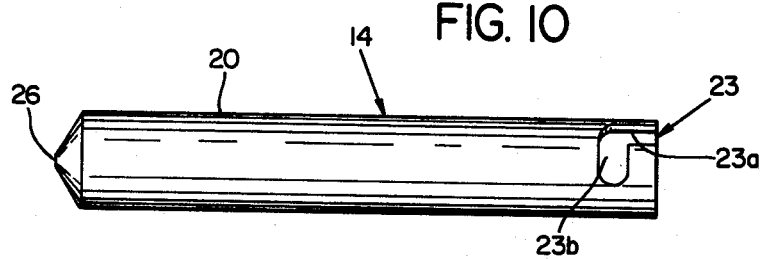

HYPODERMIC INJECTION APPARATUS

BACKGROUND AND SUMMARY OF THE INVENTION

This invention relates generally to a hypodermic injection apparatus, and more specifically to such an apparatus having a replaceable ampule unit carrying a plunger and a power source for administering intramuscular and subcutaneous injections without a needle.

Present needleless hypodermic injection apparatus involve the use of separately and independently replaceable ampule units and power source units containing $CO_2$ cartridges. An example of such a unit is described in U.S. Pat. No. 3,688,765 issued to Gasaway on Sept. 5, 1972. The device described in that patent includes a central body. On one end of the body is disposed an ampule unit having a generally cylindrical chamber and a plunger disposed in one end spaced away from a nozzle disposed in the other end. Abutting a side of the plunger opposite from the nozzle is the end of a piston which extends through a passageway to an opposite end of the body. A pressurized-gas cartridge is attached to the opposite end of the body with a frangible seal accessible from the center of the body. A firing pin is spring-loaded to be projected into the $CO_2$ cartridge for release of the gas contained therein. The firing pin is hollow to conduct escaping gas into a cylinder which houses the plunger-driving piston described earlier. The piston thus drives the plunger toward the nozzle, expelling medication contained in the ampule unit.

Such a unit requires separate loading of the pressurized-gas cartridge and the medication-containing ampule. Two members of the apparatus must be relatively rotated and axially pulled away from each other in order to cock the device. Further, the piston which drives against the plunger during ejection of the medication is exposed to the air during changing of an ampule unit. Such units thus require a fair amount of physical manipulation by the physician or other medical attendant. Also, there is some chance of infecting the ampule unit, either through its nozzle or through the plunger.

Another type of needleless hypodermic injection device is disclosed in U.S. Pat. No. 4,089,334 to Schwebel et al. This patent discloses a device which uses a pyrotechnic cap which, when detonated, provides an explosive charge of gas which drives medication through a discharge aperture in one end of the device. There are many drawbacks inherent in the use of this type of device, including danger to the patient, or at least apprehension of such danger. Because of this danger or at least the perception of such danger, this device will often not be usable in soft-tissue areas of the body, such as the mouth, where the patient may be particularly sensitive to use of an explosive device.

It is therefore a general object of the present invention to overcome the drawbacks and limitations of the prior art proposals. More particularly, the invention has as its objects, the following: (1) to provide a needleless hypodermic injection apparatus which requires only replacement of a single ampule unit containing a power source, plunger and medication ampule; (2) the provision of such an apparatus which may be operated by one having little expertise or training in the use of such devices; (3) the provision of a needleless hypodermic injector which is automatically re-cocked after each use thereof; (4) to provide a hypodermic injection apparatus having a plurality of components, which is not usable unless the components are properly and fully assembled; (5) to develop a needleless hypodermic injection device which is usable in close proximity to the soft-tissue areas of the body, such as the mouth, due to the minimization of actuation noises and expulsion of gases during the injection process; (6) the provision of an injection device which is able to inject medication into the tongue so that the medication reaches the bloodstream at the earliest possible moment; and (7) to provide a needleless hypodermic injection apparatus which is simple in construction and therefore relatively easy and inexpensive to fabricate and assemble and which therefore may be marketed in both reusable and disposable embodiments.

SUMMARY OF THE INVENTION

The present invention meets the above objects by providing a pressure-operated hypodermic injection apparatus which includes an elongate shell having inwardly facing wall means with a uniform cross-sectional configuration along a defined length thereof, and having a discharge aperture adjacent one end thereof, a plunger slideably disposed within such defined length, the plunger being shiftable between ready and spent positions disposed different distances from the aperture, a pressurized-gas cartridge mounted to the plunger to shift therewith and having gas-releasing means facing away from the .. aperture, a body mounted to the other end of the shell, and an actuator mounted to the body and manually operable for operating the gas-releasing means to drive the plunger from the ready position toward the spent position. With the plunger in the ready position, the shell and plunger define an ampule chamber capable of containing a dischargeable medication.

The gas-releasing means typically includes a frangible portion, and the actuator normally includes a reciprocable firing pin with one end designed to break the frangible portion upon contact therewith. Thus, upon actuation of the device, the firing pin breaks the frangible portion, thereby releasing the gas and driving the cartridge and plunger mounted thereto toward the aperture, discharging medication from the device and into the patient.

Means are also normally provided for selectively retaining and then releasing the firing pin so that the pin is only released upon actuation, and so that once the injector has been discharged, the pin is automatically re-cocked for subsequent use.

Another way to define the invention is as an ampule unit which is usable in a pressure-operated hypodermic injection device, but this and other aspects, features and objects of the present invention will become evident to those skilled in the art as this description continues.

BRIEF DESCRIPTION OF THE DRAWINGS

FIG. 9 is a partially sectioned, side elevation view of the apparatus; and

FIG. 10 is a side elevation view of the ampule assembly of the depicted embodiment.

DETAILED DESCRIPTION OF THE PREFERRED EMBODIMENT

Figure 1:
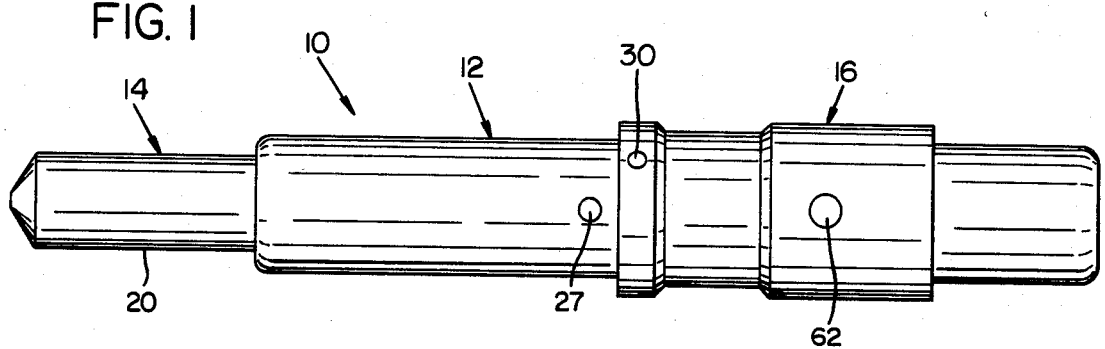
FIG. 1 is a side elevation perspective view of a hypodermic injection apparatus including an ampule unit made in accordance with the present invention.
Figure 2:
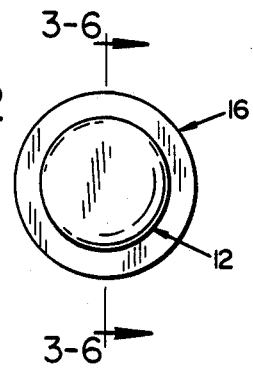
FIG. 2 is an end view of the right side of the apparatus of FIG. 1.

The drawings depict a preferred embodiment of the needleless hypodermic injection apparatus, which has been identified generally with the numeral 10. Apparatus 10 consists essentially of a body assembly 12, a removable ampule assembly 14 which is adapted to be mounted partially within the body assembly, a sliding collar 16 slideably mounted to the exterior of the body assembly, and an actuator assembly 18. Ampule assembly 14 includes a shell 20 which defines a chamber having a compressed gas-containing cartridge 22 with a plunger 24 mounted to one end. Plunger 24 includes a 1/16th inch O-ring 25 in the depicted embodiment to ensure an adequate seal between the plunger and the inner walls of shell 20. The exposed or forward end of ampule 14 includes an aperture 26 which is typically about ½ mil in diameter. Cartridge 22 is typically filled with $CO_2$ gas, although other gases may be alternatively used. A frangible cartridge seal 28, sometimes referred to herein as a frangible member, is typically fabricated of polyurethane or a similar material, and is designed to seal cartridge 22 under pressure until that seal is broken by actuator assembly 18.

As shown in FIG. 10, ampule assembly 14 is mounted to body assembly 12 by a pair of L-shaped slots 23 defined in the rearward end of shell 20, the slots being designed to receive a pair of ampule engagement pins 27 which extend from the body assembly. This structure not only provides for adequate engagement between ampule assembly 14 and body assembly 12, but also provides means to prevent discharge of apparatus 10 unless the ampule assembly is completely engaged by the body assembly. This means is depicted in FIG. 9 and includes a pair of collar pins 30 which extend inwardly through a corresponding pair of slotted or cut-out portions 32 is body assembly 12. When shell 20 of ampule assembly is pushed and then turned into body assembly 12, ampule engagement pins 27 first slide into longitudinally extending portions 23a of slots 23, and then into transverse portions 23b. Only when ampule engagement pins 27 are in abutment with the end of the transverse portions 23b will the longitudinal portions, 23a be in longitudinal alignment with collar pins 30. As will be explained more fully below, only when this longitudinal alignment exists, is it possible to slide collar 16 forwardly to discharge the apparatus.

Actuator assembly 18 includes a reciprocable portion, depicted in the figures as a firing pin 34, which includes a seal-piercing pointed projection 36 at a forward end, an axisymmetric annular groove 38 in its middle portion, and a spring seat 40 at its rearwardly disposed end. Spring seat 40 is mounted to a firing pin spring retainer 42 which encompasses and retains firing pin spring 44.

As shown in FIGS. 3-6, a plurality of firing pin retaining balls 48 are positioned within actuator assembly 18 to selectively engage and release firing pin 34 at annular groove 38. These retaining balls 48, alternatively referred to herein as retaining members or retaining rollers, are held longitudinally or axially stationary by actuator sleeve 50, within which firing pin 34 is slideably mounted. Retaining balls 48 are held against firing pin 34 by a ball retainer, which is shown generally at 52, and which sometimes will be referred to herein as inwardly facing wall means. Ball retainer 52 includes a narrowed race 54 and a broadened race 56. Narrowed race 54 is sized such that retaining balls 48 may be disposed within annular groove 38 while in abutment with that race. Broadened race 56 is sized such that retaining balls 48 may be positioned between the remaining portion of firing pin 34 and that race.

In the depicted embodiment, firing pin annular groove 38 includes rounded walls which conform to the periphery of retaining balls 48, although any converging wall configuration would suffice as long as it conforms to the configuration of the retaining member which is included in that particular embodiment. Thus, when retaining balls 48 engage annular groove 38 and are held therein by narrowed race 54, firing pin 34 is not permitted to be displaced axially either through the action of pressure within shell 20 or by the urging of firing pin spring 44. When broadened race 56 is positioned adjacent retaining balls 48, the biasing of firing spring 44 urges the balls out of annular groove 38, thus causing firing pin 34 to be displaced axially in a forward direction toward ampule assembly 14.

Ball retainer 58 is biased rearwardly by a ball retainer spring 52 which seats against an annular ring 60 in actuator sleeve 50. The rearward end of ball retainer 52 is in contact with a pair of dowel pins 62 which extend inwardly from sliding collar 16. The opposite or rearward end of dowel pins 62 seat against an inner spring 64 so that sliding collar 16 is biased forwardly by inner spring 64 and rearwardly by ball retainer spring 58. Ball retainer spring 58 exerts more force than inner spring 64 when ball retainer 52 is in the position depicted in FIGS. 3-5, for reasons which will become apparent as this description continues.

Figure 8:
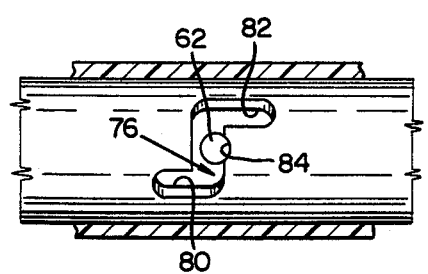
FIG. 8 is a fragmentary, partially sectioned side elevation view showing the detent safety mechanism.
Figure 7:
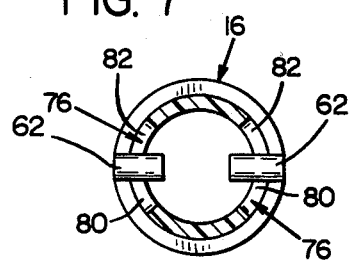
FIG. 7 is an end elevation view taken along line 7—7 of FIG. 6, except that the apparatus is rotated 90 degrees.

A bleed vent 70 through body assembly 12 and is positioned such that when ampule assembly 14 is properly engaged within the body assembly, the vent is in alignment with slot 23, as shown in FIGS. 3-6. A safety detent slot 76 is depicted in FIGS. 8 and 9. A pair of opposing slots 76 are actually provided to receive the two dowel pins 62, but only one of the slots appears in FIGS. 8 and 9. As shown in FIGS. 3-9, slot 76 includes a firing pin release portion 80 which causes actuator assembly 18 to discharge the apparatus, and a manual rearming portion 82 which re-cocks the actuator assembly prior to discharge. A centrally disposed detent portion 84 prevents collar 16 from being inadvertently rotated, because the force provided by ball retainer spring 58 is greater than inner spring 64, holding dowel pins 62 in their respective detent portions 84.

Operation of the Depicted Embodiment

In order to use injection apparatus 10, the actuator assembly 18 is first cocked. This is normally done automatically immediately following injection of medication, but may be performed manually by slightly rotating sliding collar 16 and sliding it rearwardly until dowel pins 62 have passed through the entire length of manual rearming portions 82 of the safety detent slots 76. As dowel pins 62 are being slid rearwardly with collar 16, they contact the underside of the firing pin spring 42, which causes firing pin 34 to be moved rearwardly into its cocked position depicted in FIG. 3.

With actuator assembly 18 fully cocked, the previously-spent ampule assembly 14 (if any) is then removed and a replacement assembly, having a new supply of medication and a sealed and charged cartridge 22, may be mounted into place. This is done by pushing shell 20 into body assembly 12 so that ampule engagement pins 27 slide through the longitudinally extending portions 23a of slots 23. Shell 20 is then rotated to the position shown in FIG. 9 where the ampule engagement pins 27 are in abutment with the ends of the transverse slot portions 23b. As shown in FIG. 9, with shell 20 in this position, collar pins 30 will be in alignment with the longitudinal portions 23a so that the collar is free to be subsequently slid forward to discharge the apparatus. If shell 20 has not been rotated all of the way and locked into place, such alignment will not exist.

To use the apparatus, it is positioned directly against the skin of the patient. It has been found that the depicted apparatus is particularly useful and effective when used to discharge medication into the tongue of the patient. Prior art needleless devices were typically too large, too difficult to operate, or too explosively venting to be used within the mouth. Injectors having a needle would be so painful upon injection that the patient would be likely to move his tongue, presenting the possibility of laceration. Such lacerations can be very dangerous due to the vascular nature of the tongue. This vascularity is precisely why injection directly into the tongue is so beneficial. Within seconds of injection, the medication can be in the bloodstream. This can be of critical importance in many cases.

Figure 3:
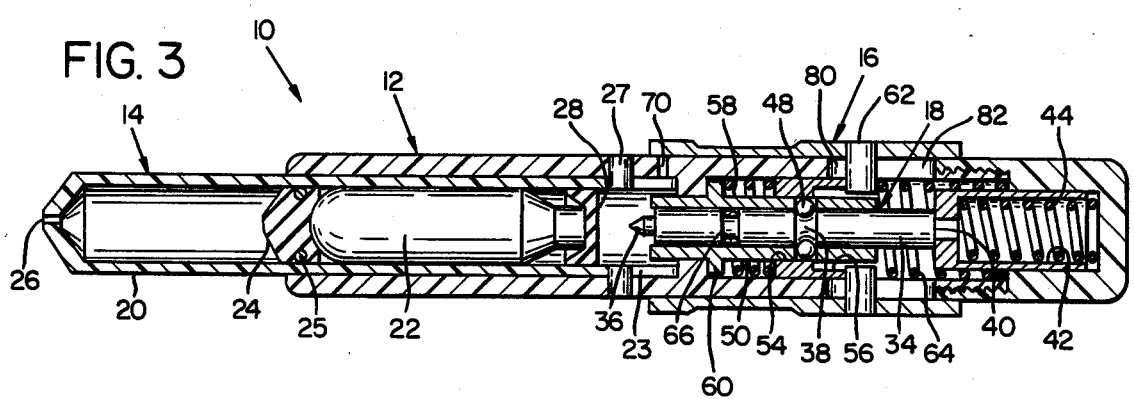
FIG. 3 is a side elevation sectional view taken along line 3–6 of FIG. 2, with the device in position ready to be activated.

FIG. 3 depicts apparatus 10 in its ready-to-be-fired mode. In this mode, narrow race 54 of ball retainer 52 holds retaining balls 48 within annular groove 38 of firing pin 34. This prevents firing pin 34 from being displaced forwardly by the biasing of firing pin spring 44.

Figure 4:
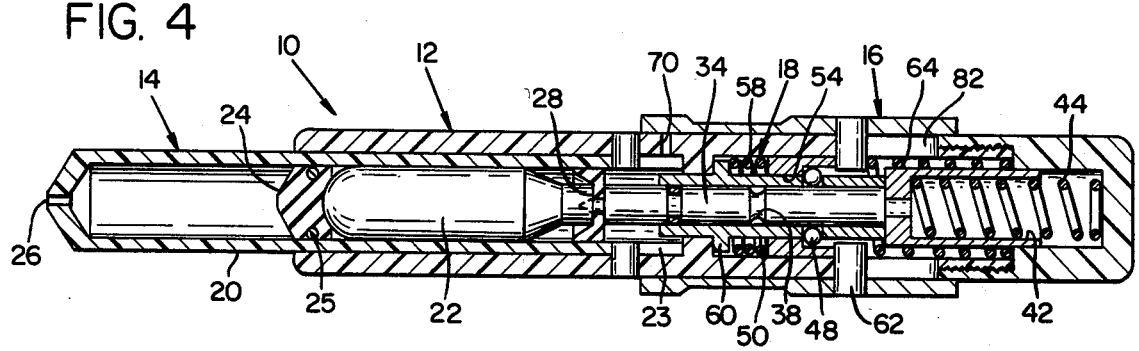
FIG. 4 is a side elevation sectional view along 3–6 of FIG. 2, corresponding to FIG. 3 except that the device is shown an instant after actuation, with a frangible seal of the cartridge being pierced, but prior to release of gas from the cartridge.

To discharge the device, the operator slides sliding collar 16 slightly forwardly so that dowel pins 78 are directed to the end of firing pin release portions 80. Again, this is not possible unless the ampule assembly 14 is fully in place and the longitudinal portions 23a of slots 23 are in alignment with the collar pins 30. This causes ball retainer 52 to be displaced forwardly against the urging of ball retainer spring 58, and positions broadened race 56 of ball retainer 52 adjacent retaining balls 48. The biasing of firing pin spring 44 causes retaining balls 48 to move radially outwardly from annular groove 38 until they are in abutment with broadened race 56, thereby freeing firing pin 34 to be axially displaced by the action of firing spring 44. This causes the projection 32 in the forward end of firing pin 34 to be driven into the frangible seal 28 in the rearward end of $CO_2$ cartridge 22, as depicted in FIG. 4.

Figure 5:
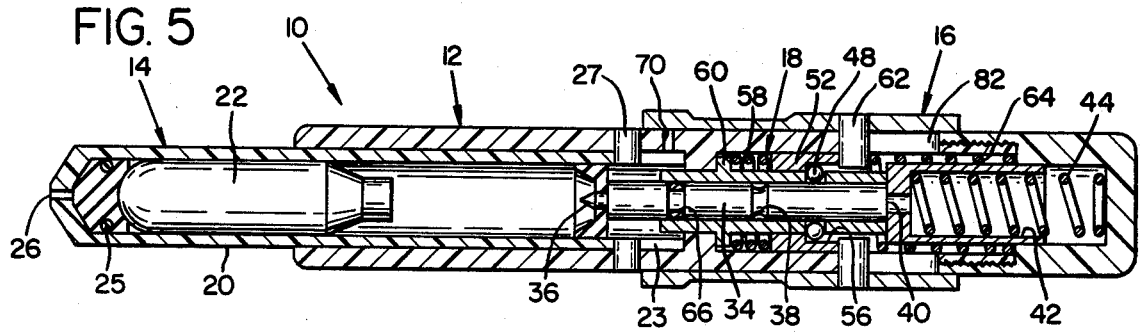
FIG. 5 is a side elevation sectional view along line 3-6 of FIG. 2, corresponding to that of FIGS. 3 and 4 except that the apparatus is shown subsequent to discharge of gas from the cartridge, at the instant the cartridge and plunger reach their spent positions.
Figure 6:
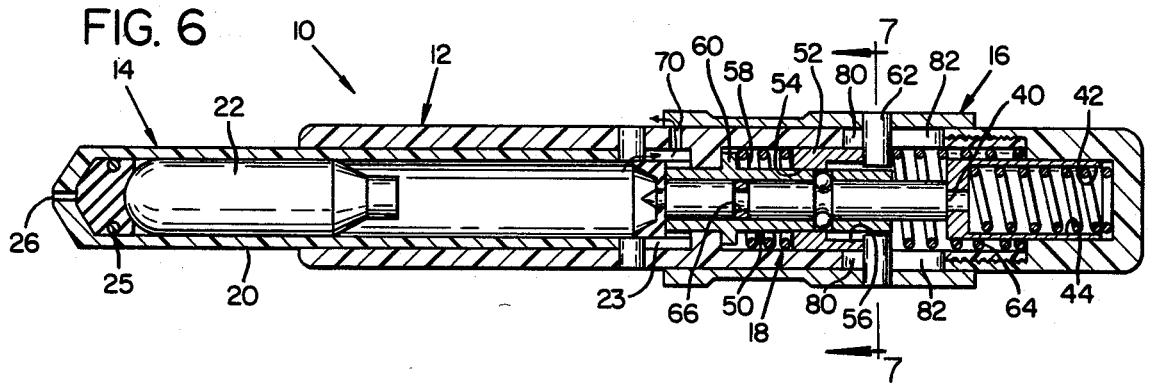
FIG. 6 is a side elevation sectional view along line 3-6 of FIG. 2, corresponding to that of FIGS. 3-5, except that the apparatus is shown a moment after the cartridge and plunger reach their spent positions, and the gases within the ampule unit have driven the firing pin back to its initial, cocked position.

The compressed gases in cartridge 22 are then free to explode outwardly in a rearward direction, thereby driving cartridge 22 and plunger 24 forwardly from their so-called "ready" position, which forces the medication through discharge aperture 26 until all of the medication is discharged and plunger 24 is disposed against the forward end of shell 20, as depicted in FIG. 5. At this point, cartridge 22 and plunger 24 are in a so-called "spent" position. With plunger 24 in this position, the pressure within shell 20 is approximately 400 psi, due to the fact that approximately 800 psi of charge is typically provided in cartridge 22. This 400 psi pressure then causes firing pin 34 to be driven rearwardly due to the action of the pressure on cartridge seal 28, against the biasing of firing pin spring 44. The force of this spring 44 is greater that the resistive force which the medication has to being driven through aperture 26, so that cartridge seal 28 remains stationary while the medication is being discharged. However, such force is substantially less than necessary to hold the firing pin in position once plunger 24 has been displaced from its ready position to its spent position depicted in FIG. 5. Therefore, the action of the 400 psi on cartridge seal 28 causes firing pin 34 to be driven rearwardly to the position depicted in FIG. 6, thus automatically re-cocking actuator assembly 18. The dislodgement of cartridge seal 28 is not immediate, due to the resistance provided by firing pin spring 44, so it is not typically fully effected until apparatus 10 would be removed from proximity to the patient's body. Once firing pin 34 is re-cocked, the pressurized gas within shell 20 is free to exit through one of the slots 23 in shell 20 and bleed vent 70 in body assembly 12, and then out to the atmosphere due to clearance between collar 16 and body assembly 12, all as shown in FIG. 6.

Thus, the device automatically re-cocks itself for the next operation. The ampule assembly 14 may then be removed, and be replaced with a freshly charged cartridge 22 and a new portion of medication, for the next use.

While the invention has been particularly shown and described with reference to the foregoing preferred embodiment, it will be understood by those skilled in the art that other changes in form and detail may be made therein without departing from the spirit and scope of the invention as defined in the following claims.

It is claimed and desired to be secured by Letters Patent:

1. In a pressure-operated hypodermic injection apparatus including a body and an actuator mounted on the body, a replaceable, medication-discharging ampule unit comprising:
   an elongate shell having inwardly facing wall means characterized by a substantially uniform cross-sectional configuration along a defined length portion of said shell, said shell further defining a discharge aperture adjacent a forward end thereof;
   a plunger slideably and sealingly disposed within said define length portion in said shell, displaceable between a rearward, ready position, spaced one distance from said aperture, and a forward, spent position closer to said aperture than said ready position;

said shell and plunger, with the latter in said ready position defining an ampule chamber capable of containing dischargeable medication; and a compressed-gas containing cartridge operable under the influence of the apparatus actuator to drive said plunger and reciprocate with said plunger from said ready position toward said spent position.

2. In a pressure-operated hypodermic injection apparatus including a body and an actuator mounted on the body, a replaceable, medication-discharging ampule unit comprising:

an elongate shell having inwardly facing wall means characterized by a substantially uniform cross-sectional configuration along a defined length portion of said shell, said shell further defining a discharge aperture adjacent a forward end thereof;

a plunger slideably and sealingly disposed within said defined length portion in said shell, displaceable between a rearward, ready position, spaced one distance from said aperture, and a forward, spent position closer to said aperture than said ready position;

said shell and plunger, with the latter in said ready position, defining an ampule chamber capable of containing dischargeable medication; and a compressed-gas containing cartridge including means for releasing its gas charge in a rearward direction upon actuation by the actuator to drive said plunger from said ready position toward said spent position.

3. The ampule unit of claim 2 wherein said cartridge includes a frangible member which is broken upon actuation by the actuator.

4. The ampule unit of claim 2 wherein said cartridge is mounted to said plunger within said shell and slides therewith between said ready and spent positions.

5. The ampule unit of claim 2, further comprising:
means for being rotatably mounted to the apparatus; and
means for preventing operation of the actuator and displacement of said plunger unless said ampule unit is all of the way turned into the apparatus.

6. The ampule unit of claim 5, wherein said means for preventing operation comprises longitudinally extending recess means defined in said shell for receiving, upon actuation, a complementing extension member of the actuator, said recess means being rotationally aligned with the extension member only when the ampule unit is turned all of the way into the apparatus.

7. A pressure-operated hypodermic injection apparatus comprising:

an elongate shell having inwardly facing wall means characterized by a substantially uniform cross-sectional configuration along a defined length portion of said shell, said shell further defining a discharge aperture adjacent one end thereof;

a plunger slideably and sealingly disposed within said defined length portion in said shell, shiftable from a ready position spaced one distance from said aperture toward a spent position closer to said aperture than said ready position;

said shell and plunger, with the latter in said ready position, defining an ampule chamber capable of containing dischargeable medication;

a pressurized-gas cartridge mounted to said plunger to shift therewith and having gas-releasing means facing away from said discharge aperture;

a body sealingly and releasably joined to another end of said shell; and an actuator mounted on said body and manually operable for selectively operating said gas-releasing means to drive said plunger from said ready position toward said spent position.

8. The apparatus of claim 7 wherein said actuator includes a reciprocable portion which is displaceable between retracted and extended positions.

9. The apparatus of claim 8 wherein said reciprocable portion includes a reciprocable firing pin having one end which faces said gas-releasing means, and which comes into contact with said gas-releasing means upon being displaced to said extended position.

10. The apparatus of claim 9 wherein said gas-releasing means includes a frangible portion and said one end of said reciprocable firing pin includes means for breaking said frangible portion upon contact therewith.

11. The apparatus of claim 9 wherein said firing pin includes an annular groove therein, and wherein said actuator includes a plurality of retaining rollers which selectively enter into engagement with said firing pin annular groove, an inwardly facing portion with a narrow race and a broadened race for selectively holding said rollers in engagement with said groove, and permitting said rollers to move out of said groove, respectively, to hold and then release said firing pin.

12. A pressure-operated hypodermic injection apparatus comprising:

an ampule unit having an elongate shell with wall means defining an internal chamber and a discharge aperture adjacent one end thereof, a plunger slideably and sealingly disposed within the chamber shiftable between a ready position spaced one distance from said aperture and a spent position closer to said aperture than the ready position, and a pressurize-gas cartridge slidingly disposed in said shell fixed to said plunger opposite from said aperture, said cartridge having a frangible seal on a side opposite from said aperture and accessible from the other end of said shell;

an elongate body releasably fixedly and sealingly joinable at one end to the other end of said shell of said ampule unit, said body having a longitudinal passageway having an opening disposed adjacent said cartridge seal;

a firing pin slidingly disposed in said passageway with a seal-fracturing end disposed adjacent said one opening of said passageway, said pin being shiftable from a cocked position remote from said seal to a fired position with said one end of said pin extending through said seal when said ampule unit is joined to said body with said plunger in said ready position;

pin biasing means mounted in said body and joined to said pin for urging said pin from said cocked position toward said fired position;

arming means for positioning said pin in said cocked position; and trigger means for retaining said pin in said cocked position and for selectively releasing said pin for traveling toward said fired position.

13. The apparatus of claim 12 wherein said body includes a longitudinally displaceable inwardly facing portion, and wherein said trigger means comprises:
an annular groove defined in said pin;
a plurality of pin retaining members positioned and sized to selectively enter into engagement with said pin annular groove, said members being in contact with said inwardly facing portion of said body, and wherein said inwardly facing portion includes narrowed race means for holding said members in engagement with said annular groove, and broadened race means for allowing said members to be displaced from said annular groove; and means for preventing longitudinal displacement of said members so that said pin is held from displacement in said cocked position when said members engage said annular groove and said pin is released to be displaced toward said fired position when said members release said pin.

14. The apparatus of claim 13 wherein said annular groove presents a centrally-converging, inclined abutment surface to said pin retaining members so that when said members are not held in engagement with said annular groove by said narrowed race means, the action of said spring means causes said retaining members to be displaced outwardly along said abutment surface until said pin is free to move toward said fired position.

15. The apparatus of claim 14 wherein said retaining members comprise generally spherical rollers.

16. The apparatus of claim 15 wherein said broadened race means is disposed remote from said ampule unit with respect to said narrowed race means, and further comprising race biasing means for urging said race means away from said ampule unit, and wherein said arming means includes a collar slidably mounted to said body, said collar contacting said inwardly facing body portion to permit said portion to be displaced against the urging of said race biasing means to thereby control the operation of said retaining members.

17. The apparatus of claim 12 wherein said firing pin includes means for engaging said frangible seal when said firing pin is in said fired position, and said pin biasing means urges said pin toward said fired position with a force less than that within said shell after said seal has been broken and said plunger has been driven to said spent position, so that after said plunger is driven to said spent position, said frangible seal and pin are driven toward said cocked position, and wherein said trigger means includes means for re-engaging said pin once it has been driven back to said cocked position.

18. The apparatus of claim 17 wherein said means for re-engaging said pin comprises said pin retaining members.

19. A pressure-operated, needleless hypodermic injection apparatus for injecting medication into the tongue of a patient, comprising:

a replaceable, medication-discharging ampule unit which includes an elongate shell defining a discharge aperture adjacent a forward end thereof, a plunger slideably and sealingly disposed within said shell, displaceable between a readly position spaced one distance from said aperture and a spent position closer to said aperture than said ready position, said shell and plunger defining an ampule chamber capable of containing the medication when said plunger is in said ready position, and pressurized-gas means for driving said plunger and having gas-releasing means facing away from said discharge aperture; and means for manually actuating said ampule unit upon contact with the tongue of the patient, said means being mounted to said ampule unit and being operatable for selectively operating said plunger-driving means to drive said plunger from said ready position toward said spent position.

20. The apparatus of claim 19, wherein said means for manually actuating said ampule unit comprises:
a body sealingly and releasably joined to another end of said shell; and
an actuator mounted on said body and manually operable for selectively operating said gas-releasing means to drive said plunger from said ready position toward said spent position, and including a reciporocable portion displaceable between retracted and extended positions, said reciprocable portion including a reciprocable firing pin having one end facing said gas-releasing means which comes into contact with said gas releasing means upon being displaced to said extended position.

21. The apparatus of claim 20, wherein said gas-releasing means includes a frangible portion and said one end of said reciprocable firing pin includes means for breaking said frangible portion upon contact therewith.

22. The apparatus of claim 20, wherein said firing pin includes an annular groove therein, and wherein said actuator includes a plurality of retaining rollers which selectively enter into engagement with said firing pin annular groove, an inwardly facing portion with a narrow race and a broad race for selectively holding said rollers in engagement with said groove, and permitting said rollers to move out of said groove, respectively, to hold and then release said firing pin.

23. A pressure-operated hypodermic injection apparatus comprising:
an elongate shell having inwardly facing wall means and defining a discharge aperture adjacent one ene thereof;
a plunger slideably and sealingly disposed within said shell, shiftable from a ready position spaced one distance from said aperture toward a spent position closer to said aperture;
said shell and plunger, with the latter in said ready position, defining an ampule chamber capable of containing dischargeable medication; and
pressurized-gas means for driving said plunger and having gas-releasing means facing away from said discharge aperture.

24. The apparatus of claim 23, further comprising:
a body sealingly and releasably joined to another end of said shell; and
an actuator mounted on said body and manually operable for selectively operating said gas-releasing means to drive said plunger from said ready position toward said spent position, and including a reciprocable portion displaceable between retracted and extended positions, said reciprocable portion including a reciprocable firing pin having one end facing said gas-releasing means which comes into contact with said gas releasing means upon being displaced to said extended position.

25. The apparatus of claim 24, wherein said gas-releasing means includes a frangible portion and said one end of said reciprocable firing pin includes means for breaking said frangible portion upon contact therewith.

26. The apparatus of claim 24, wherein said firing pin includes an annular groove therein, and wherein said actuator includes a plurality of retaining rollers which selectively enter into engagement with said firing pin annular groove, an inwardly facing portion with a narrow race and a broadened race for selectively holding said rollers in engagement with said groove, and permitting said rollers to move out of said groove, respectively, to hold and then release said firing pin.

27. A pressure-operated hypodermic injection apparatus for use with a medication-containing ampule having a discharge aperture adjacent a forward end thereof, and a pressurized-gas cartridge with a frangible gas-releasing portion facing away from said discharge aperture, wherein the injection apparatus comprises:
- a body for sealing and releasably engaging the ampule; and
- an actuator mounted to said body and manually operable for selectively operating the gas-releasing member, said actuator including a reciprocable portion which is displaceable between retracted and extended positions and includes a reciprocable firing member having one end for facing the ampule gas cartridge frangible portion, and which comes into contact with the frangible gas-releasing portion upon being displaced to said extended portion, said reciprocable firing member including means for breaking the frangible gas-releasing portion upon contact therewith.

28. The apparatus of claim 27, wherein said firing member includes a annular groove therein, and wherein said actuator includes a plurality of retaining rollers which selectively enter into engagement with said firing member annular groove, an inwardly facing portion with a narrow race and a broad race for selectively holding said rollers in engagement with said groove, and permitting said rollers to move out of said groove, respectively, to hold and then release said firing member.

29. The apparatus of claim 27, further comprising the medication-containing ampule.

* * * * *